United States Patent [19]
Oura et al.

[11] Patent Number: 5,358,962
[45] Date of Patent: Oct. 25, 1994

[54] ANTIHYPERTENSIVE METHOD

[75] Inventors: Hikokichi Oura, Toyama; Itsuo Nishioka, Fukuoka; Takako Yokozawa, Toyama; Tadao Takeuchi, Yamato, all of Japan

[73] Assignee: Minophagen Pharmaceutical Company, Tokyo, Japan

[21] Appl. No.: 51,942

[22] Filed: Apr. 22, 1993

[51] Int. Cl.$^5$ ............................................. A61K 31/34
[52] U.S. Cl. ...................................................... 514/469
[58] Field of Search ........................................ 541/469

[56] References Cited
PUBLICATIONS

Yokozawa, T. et al., "Magnesium Lithospermate B Suppressed the Proliferation of Mesangial Cells", *Journal of Medical and Pharmaceutical Society for WAKAN-YAKU*, vol. 9, 165–168, 1992.

Yokozawa, T. et al., "Effect of Magnesium Lithospermate B on the Renal and Urinary Kallikrein Activities in Rats and Adenine-Induced Renal Failure", *Japanese Journal of Nephrology*, vol. 35, No. 4, 1993.

Yokozawa, T. et al., "Inhibitory Effects of Crude Drug Components on the Proliferation of cultured Human Mesangial Cells", *Japanese Journal of Nephrology*, vol. 35, No. 4, 1993.

Yokozawa, T. et al., "Contribution of Prostaglandins to the Renal Responses to Magnesium Lithospermate B Isolated from Salviae Miltiorrhizae Radix", *Chem. Pharm. Bull.*, 37(6) 1568–1571, vol. 37, No. 6, 1989.

*Primary Examiner*—Jerome D. Goldberg
*Attorney, Agent, or Firm*—Knobbe Martens Olson & Bear

[57] ABSTRACT

An antihypertensive method comprising administering to a hypertensive patient a pharmaceutical agent containing lithospermic acid B represented by the formula:

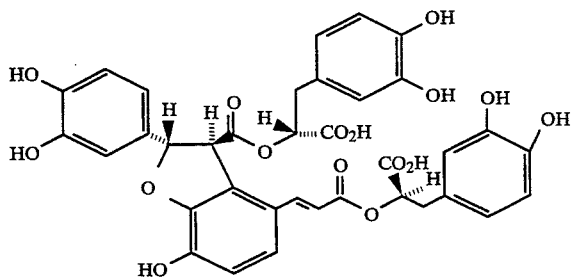

and/or the pharmaceutically acceptable salt thereof, for example, $Mg^{2+}$, $K^+$, $NH_4^+$ and $Ca^{2+}$ salts thereof, as an effective ingredient.

4 Claims, No Drawings

ANTIHYPERTENSIVE METHOD

BACKGROUND OF THE INVENTION

The present invention relates to an antihypertensive method comprising administering to a patient a pharmaceutical agent containing lithospermlc acid B and the pharmaceutically acceptable salt thereof as the effective ingredients. Lithospermic acid B and the pharmaceutically acceptable salt thereof are contained in a Chinese and Japanese traditional medicine, Salvia miltiorrhiza Bunge. As is described in Japanese Patent Laid-open Publication No. Hei 1-268682 (1989) (the applicant and the inventors are the same as in the present invention, respectively), the present inventors have extracted lithospermic acid B in water From the root of Salvia miltiorrhiza Bunge in water and isolated by chromatography on a column filled with packing agents, a porous gel carrier and Sephadex(trade mark; manufactured by Pharmacia, Co. Ltd.; the same shall apply hereinbelow). Then, the inventors have accomplished the analysis of the steric chemical structure. Simultaneously, the inventors have examined whether or not lithospermlc acid B has all action to improve a renal function, and have provided a method for producing a renal function-improving pharmaceutical agent to decrease uremigenic substances in a rat with an adenine induced renal impairment as well as a method for producing the salt of lithospermic acid B.

It has been known conventionally that Salvia miltiorrhiza Bunge has vasodilating and antihypertensive actions. The present inventors have made further investigations to elucidate what actions as a pharmaceutical agent for use in the disease of cardiovascular system may be exhibited with lithospermic acid B per se, as an isolated substance from Salvia miltiorrhiza Bunge, and with the pharmaceutically acceptable salt thereof. Consequently, the inventors have firstly found that the salt of lithospermlc acid B has a distinctive antihypertensive action. Thus, the present invention has been achieved.

SUMMARY OF THE INVENTION

The compound to be used in the present invention is lithospermic acid B represented by the formula:

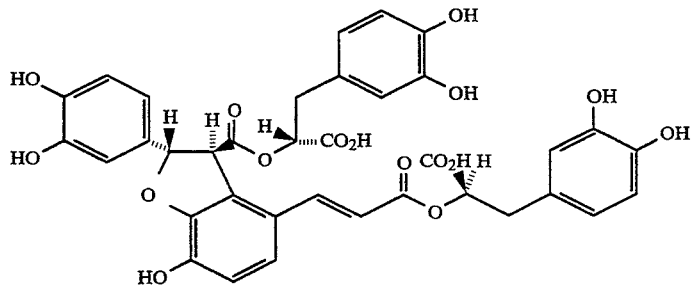

and the pharmaceutically acceptable salt thereof. The pharmaceutical acceptable salt includes magnesium (abbreviated as "Mg" hereinbelow) salt, potassium (abbreviated as "K" hereinbelow) salt, ammonium (abbreviated as "NH4" hereinbelow) salt, calcium (abbreviated as "Ca" hereinbelow) salt, and the like.

Of these salts, the Mg salt, K salt, NH4 salt and Ca salt of lithospermic acid B can be represented by the general formula:

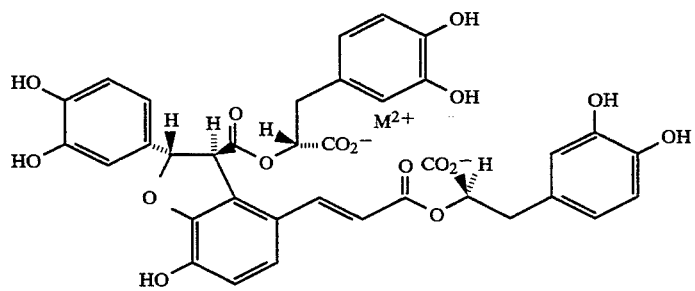

(wherein $M^{2+}$ represents $Mg^{2+}$, $K^+$, $NH_4^+$ or $Ca^{2+}$).

These compounds can be obtained by separating a specific fraction from the extract of Salvia miltiorrhiza Bunge by column chromatography. For example, the extract of Salvia miltiorrhiza Bunge is adjusted to pH 2 to 4, which is then applied to column chromatography, followed by washing with water. After passing an aqueous solution of acetate such as calcium acetate or magnesium acetate through the column prior to washing with water, a fraction is eluted with aqueous methanol, which is separated and purified to isolate lithospermic acid B.

The Mg salt and (K+NH4) salt of lithospermic acid B can be obtained by applying the extract of Salvia miltiorrhiza Bunge to column chromatography, thereby separating a fraction containing the main spot under monitoring with thin-layer chromatography, further separating a fraction containing the main spot by column chromatography under monitorring with thin-layer chromatography.

In order to examine the pharmacological effect of these compounds as a pharmaceutical agent for use in the disease of cardiovascular system, as will be described below, tests for antihypertensive actions were done as follows: a test in normal rats, a test in rats with an adenine-induced renal impairment, a test in rats with an adenine-induced renal impairment which rats are administered 4% saline, and a test in spontaneously hypertensive rats. Consequently, the antihypertensive action of the compound in accordance with the present invention is distinctively demonstrated. Thus, the compound is extremely useful as antihypertensives.

As a pharmaceutical agent, the compound of the present invention can be used in the form as it is. Methods for the administration of the compound are selected from any of oral administration and parenteral administration, and the dosage of the compound varies depending on the symptoms, age, etc. of a patient, but generally, the compound is administered to a light or moderate hypertensive adult patient at a dose within the range of 50 to 1500 mg/day so that the expected effect can be expected.

In accordance with the present invention, an oral pharmaceutical agent can be prepared in the form of powders, granules, sugar coated tablets, tablets and capsules according to the conventional methods, by mixing the compound with one or more pharmaceutically acceptable, non-toxic excipients, for example, lactose, potato starch, sodium hydrogen carbonate, sodium alginate, magnesium silicate, calcium carbonate, hydroxypropyl cellulose, synthetic aluminum silicate, crystalline cellulose and the like.

Because the salt of lithospermic acid B is readily soluble in water, the salt can be prepared in the form of injections as a parenteral pharmaceutical agent. For injections, pharmaceutically acceptable isotonization agents, for example, physiological saline or 5% glucose solution, and pH adjusters may be added to the salt for preparing a pharmaceutical formulation according to the conventional methods.

EXAMPLE

Pharmaceutical formulation examples of the compound to be used in the present invention will be explained firstly.

| Formulation example | |
| --- | --- |
| Mg salt of lithospermic acid B | 200 g |
| Precipitated calcium carbonate | 200 g |
| Crystalline cellulose | 300 g |
| Talc | 10 g |
| Lactose | 490 g |
| Total | 1200 g |

The above composition was prepared in the form of tablets having a weight of 240 mg/tablet according to the conventional methods.

Explanation will follow about the examples of the pharmacological tests of the salt of lithospermic acid B. The antihypertensive action of the compound of the present invention was significantly indicated In these tests.

Pharmacological Test

<Test Example 1>

Antihypertensive test of the Mg salt of lithospermic acid B in normal rats:

Male Wistar rats (body weight; about 200 g) were fed with 18% casein diet (18% of protein, 72.9% of carbohydrate, 2% of fat, 1% of mixed vitamins, 4% of mixed salts, 2% of cellulose powder, and 0.1% of choline chloride) along with water ad libitum in a chamber maintained at a constant temperature and humidity (23° C., RH 60%) and at a 12 hr cycle of light and darkness. Blood pressure was measured with a non-invasive blood pressure meter (manufactured by Muromachi Kikai). Systolic blood pressure, mean blood pressure and diastolic blood pressure of the rats under no anesthesia were measured by tail-cuff method. The test rats were orally administered the Mg salt of lithospermic acid B dissolved in water every day. Control rats were treated in the same way as in tile test rats except that Mg salt of lithospermic acid B was not administered. Results are shown in Table 1.

TABLE 1

| Duration (day) | Dose of Mg salt of lithospermic acid B (/kg body weight) | Systolic pressure | Mean pressure | Diastolic pressure |
| --- | --- | --- | --- | --- |
| 6 | Control 0 | 147.1 ± 3.4 (100) | 113.0 ± 2.4 (100) | 95.6 ± 3.4 (100) |
|  | 10 mg | 153.6 ± 5.2 (104) | 114.2 ± 3.2 (101) | 94.3 ± 2.3 (99) |
| 18 | Control 0 | 139.4 ± 3.1 (100) | 113.8 ± 2.3 (100) | 100.7 ± 2.3 (100) |
|  | 10 mg | 137.9 ± 2.9 (99) | 109.0 ± 1.7 (96) | 94.4 ± 2.0 (94) |

Numerical Value represent "average ± standard deviation" of 10 rats. Value in parentheses indicate ratio of pressure of test rat to control in percentage.

<Test Example 2>

Antihypertensive test of Mg salt of lyso-spermic acid B in rats with an adenine induced renal Impairment:

The rats were fed for 24 days with a synthetic diet composed of the diet of Test Example 1 and 0.75% of adenine added thereto, The Mg salt of lithospermic acid was orally administered every day, Blood pressure was measured in the same manner as in Test Example 1, Results are reported in Table 2,

TABLE 2

| Duration (day) | Dose of Mg salt of lithospermic acid B (/kg body weight) | Systolic pressure | Mean pressure | Diastolic pressure |
| --- | --- | --- | --- | --- |
| 12 | Control 0 | 162.7 ± 6.0 (100) | 129.3 ± 3.0 (100) | 112.3 ± 2.7 (100) |
|  | 10 mg | 153.8 ± 4.2 (95) | 119.9 ± 3.1[a] (93) | 102.1 ± 3.0[a] (91) |
| 24 | Control | 175.8 ± 4.5 | 136.7 ± 2.6 | 117.0 ± 3.3 |

TABLE 2-continued

| Duration (day) | Dose of Mg salt of lithospermic acid B (/kg body weight) | Systolic pressure | Mean pressure | Diastolic pressure |
|---|---|---|---|---|
| | 0 | (100) | (100) | (100) |
| | 10 mg | 167.3 ± 4.6 (95) | 125.5 ± 2.8[b] (92) | 104.3 ± 2.4[b] (89) |

Significant difference; [a]$P < 0.05$; [b]$p < 0.01$.
Numerical value represents "average ± standard deviation" of 10 rats.

<Test Example 3>

Antihypertensive test of Mg salt of lithospermic acid B in 4% saline-administered-rats with an adenine induced renal impairment:

The rats were fed for 24 days with a synthetic diet composed of the diet of Test Example 1 and 0.75% of adenine and 4% NaCl added thereto. The Mg salt of lithospermic acid B was orally administered every day, and blood pressure was measured in the same manner as in Test Example 1. Results are shown in table 3.

TABLE 3

| Duration (day) | Dose of Mg salt of lithospermic acid B (/kg body weight) | Systolic pressure | Mean pressure | Diastolic pressure |
|---|---|---|---|---|
| 12 | Control 0 | 192.9 ± 7.6 (100) | 150.5 ± 6.6 (100) | 129.1 ± 6.4 (100) |
| | 5 mg | 181.9 ± 6.1 (94) | 131.4 ± 5.3[a] (87) | 106.0 ± 6.3[a] (82) |
| | 10 mg | 170.4 ± 5.2[a] (88) | 130.4 ± 3.9[a] (87) | 110.3 ± 3.8[a] (85) |
| 24 | Control 0 | 208.7 ± 9.4 (100) | 167.4 ± 7.8 (100) | 146.5 ± 7.3 (100) |
| | 5 mg | 190.3 ± 6.1 (91) | 144.8 ± 6.5[a] (86) | 121.8 ± 7.3[a] (83) |
| | 10 mg | 184.7 ± 5.2[a] (88) | 147.0 ± 3.9[a] (88) | 128.0 ± 4.6[a] (87) |

Significant difference; [a]$P < 0.05$.
Numerical value represents "average ± standard deviation" of 10 rats.

<Test Example 4>

Antihypertensive test of Mg salt of lithospermic acid in SHR(spontaneously hypertensive rats) as genetically hypertensive animal model.

Male SHR, weighed about 200 g and aged 8 weeks, were fed with a diet for feeding rats (the trade mark of the diet: CE-2; manufactured by Nippon Claire Company). The Mg salt of lithospermic acid B was orally administered to the rats every day, and the blood pressure was measured in the same manner as in Test Example 1. Results are shown in Table 4.

TABLE 4

| Duration (day) | Dose of Mg salt of lithospermic acid B (/kg body weight) | Systolic pressure | Mean pressure | Diastolic pressure |
|---|---|---|---|---|
| 0 | Control 0 | 194.0 ± 4.3 (100) | 148.8 ± 4.5 (100) | 124.9 ± 5.1 (100) |
| | 5 mg | 192.1 ± 4.5 (99) | 146.7 ± 4.3 (99) | 125.8 ± 4.1 (101) |
| | 10 mg | 193.8 ± 5.3 (100) | 150.2 ± 5.7 (101) | 130.2 ± 5.9 (104) |
| 6 | Control 0 | 206.6 ± 6.8 (100) | 161.4 ± 5.0 (100) | 138.5 ± 4.4 (100) |
| | 5 mg | 198.4 ± 3.1 (96) | 152.1 ± 2.6 (94) | 128.8 ± 2.8 (93) |
| | 10 mg | 191.6 ± 4.3 (93) | 152.8 ± 3.8 (95) | 133.2 ± 3.8 (96) |
| 12 | Control 0 | 223.7 ± 4.0 (100) | 173.0 ± 3.2 (100) | 147.4 ± 3.2 (100) |
| | 5 mg | 212.6 ± 6.9 (95) | 164.3 ± 4.1 (95) | 140.0 ± 3.5 (95) |
| | 10 mg | 206.7 ± 6.0[a] (92) | 158.6 ± 4.7[a] (92) | 134.3 ± 4.3[a] (91) |
| 18 | Control 0 | 223.8 ± 4.9 (100) | 177.4 ± 4.7 (100) | 151.7 ± 5.4 (100) |
| | 5 mg | 211.4 ± 5.9 (94) | 163.6 ± 3.9[a] (92) | 136.4 ± 3.4[a] (90) |
| | 10 mg | 207.9 ± 4.7[a] (93) | 164.4 ± 3.6[a] (93) | 141.4 ± 3.1 (93) |
| 24 | Control 0 | 230.1 ± 5.4 (100) | 178.1 ± 4.1 (100) | 151.8 ± 4.5 (100) |
| | 5 mg | 206.0 ± 5.3[b] (90) | 157.0 ± 4.6[b] (88) | 132.3 ± 5.3[b] (87) |
| | 10 mg | 206.3 ± 6.4[b] (90) | 154.7 ± 5.9[b] (87) | 127.0 ± 6.1[b] (84) |

TABLE 4-continued

| Duration (day) | Dose of Mg salt of lithospermic acid B (/kg body weight) | Systolic pressure | Mean pressure | Diastolic pressure |
|---|---|---|---|---|
| 36 | Control 0 | 232.3 ± 6.4 (100) | 187.2 ± 4.7 (100) | 164.3 ± 4.8 (100) |
|  | 5 mg | 218.3 ± 7.3 (94) | 168.3 ± 6.2$^a$ (90) | 143.1 ± 6.6$^a$ (87) |
|  | 10 mg | 207.1 ± 6.4$^b$ (89) | 158.6 ± 5.7$^c$ (85) | 134.0 ± 6.1$^c$ (82) |
| 48 | Control 0 | 236.2 ± 5.8 (100) | 182.0 ± 6.0 (100) | 157.8 ± 5.8 (100) |
|  | 5 mg | 212.0 ± 8.2$^a$ (90) | 161.8 ± 6.0$^a$ (89) | 136.4 ± 5.1$^a$ (86) |
|  | 10 mg | 203.2 ± 9.6$^b$ (86) | 155.1 ± 6.7$^b$ (85) | 130.8 ± 5.5$^b$ (83) |
| 60 | Control 0 | 240.0 ± 5.9 (100) | 200.5 ± 4.5 (100) | 180.5 ± 4.5 (100) |
|  | 5 mg | 215.0 ± 9.2$^a$ (90) | 176.3 ± 8.5$^a$ (88) | 154.4 ± 7.7$^b$ (86) |
|  | 10 mg | 205.2 ± 10.5$^b$ (86) | 163.4 ± 8.9$^c$ (81) | 142.2 ± 8.1$^c$ (79) |

Significant difference; $^aP < 0.05$; $^bp < 0.01$; $^cp < 0.001$.
Numerical value represents "average ± standard deviation" of 10 rats.

<Test Example 5>

Acute Toxicity Test $LD_{50}$ of the Mg salt of lithospermic acid B according to Up and Down method was measured. The term $LD_{50}$ means 50% lethal dose hereinbelow. The results are as follows.

1. Intraperitoneal administration $LD_{50}$ of the Mg salt of lithospermic acid B>2195 mg/kg (ddy male mouse, 6 weeks age, body weight: 31 to 34 g)

2. Oral administration $LD_{50}$ of the Mg salt of lithospermic acid B>3000 mg/kg (ddy male mouse, 6 weeks age, body weight: 31 to 35 g)

What is claimed is:

1. An antihypertensive method comprising the step of administering to a hypertensive patient an effective anti-hypertensive amount of a pharmaceutical agent comprising a compound selected from the group consisting of lithospermic acid B represented by the formula:

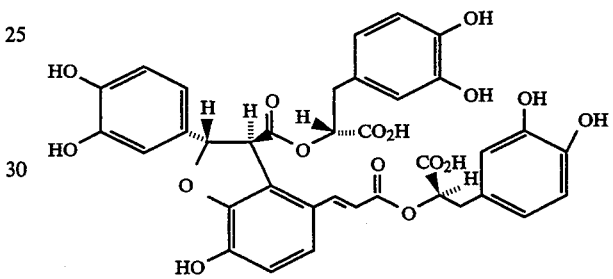

and a pharmaceutically acceptable salt thereof as effective ingredient.

2. The method according to claim 1, wherein the pharmaceutically acceptable salt of lithospermic acid B is selected from the group consisting of $Mg^{2+}$, $K^+$, $NH_4^+$, and $Ca^{2+}$ salts of lithospermic acid B.

3. A method according to claim 1, wherein the agent is selected from the group consisting of an oral pharmaceutical agent and a parenteral pharmaceutical agent.

4. A method according to claim 1, wherein said effective antihypertensive amount is a dose of from about 50 mg/day to to about 1500 mg/day.

* * * * *